(12) United States Patent
Gillman

(10) Patent No.: US 10,722,309 B2
(45) Date of Patent: Jul. 28, 2020

(54) METHODS TO ASSIST WITH MEDICAL PROCEDURES BY UTILIZING PATIENT-SPECIFIC DEVICES

(71) Applicant: Bullseye Hip Replacement, LLC, Las Vegas, NV (US)

(72) Inventor: Michael Gillman, Laguna Beach, CA (US)

(73) Assignee: Bullseye Hip Replacement, LLC, Laguna Beach, CA (US)

( * ) Notice: Subject to any disclaimer, the term of this patent is extended or adjusted under 35 U.S.C. 154(b) by 192 days.

(21) Appl. No.: 15/643,847

(22) Filed: Jul. 7, 2017

(65) Prior Publication Data

US 2018/0008349 A1    Jan. 11, 2018

Related U.S. Application Data

(60) Provisional application No. 62/360,828, filed on Jul. 11, 2016.

(51) Int. Cl.
*A61B 34/10* (2016.01)
*A61B 17/70* (2006.01)
(Continued)

(52) U.S. Cl.
CPC .......... *A61B 34/10* (2016.02); *A61B 17/1785* (2016.11); *A61B 17/7059* (2013.01);
(Continued)

(58) Field of Classification Search
CPC .......... A61B 17/7062; A61B 2017/568; A61B 34/10; A61B 2/4684
See application file for complete search history.

(56) References Cited

U.S. PATENT DOCUMENTS 5,916,220 A * 6/1999 Masini ................. A61B 17/155
606/87
6,712,856 B1 * 3/2004 Carignan ............... A61B 34/10
623/20.35
(Continued)

FOREIGN PATENT DOCUMENTS

WO    WO-9325157 A1    12/1993
WO    WO-2018/013416 A1    1/2018

OTHER PUBLICATIONS

International search report and written opinion dated Nov. 17, 2017 for PCT Application US-2017041043.

*Primary Examiner* — David W Bates
(74) *Attorney, Agent, or Firm* — FisherBroyles, LLP

(57) ABSTRACT

Patient-specific systems and methods are provided for assisting in medical procedures, and can include producing patient-specific devices from computer models of a patient's anatomy, including a first patient-specific device configured to identify and allow access to a resection area in an operation location for a medical procedure; a second patient-specific device configured to refine the procedure, following use of the first patient-specific device and in some embodiments, to identify and allow access to installation locations for an implant and/or surgical hardware; and/or a third patient specific device configured to assist in confirming placement of the implant and/or surgical hardware and refining the procedure, following use of the first and second patient-specific devices. Each of these devices may be developed from patient-specific computer model data via patient-specific image data and may enhance a variety of procedures.

13 Claims, 16 Drawing Sheets

(51) Int. Cl.
  *A61F 2/46* (2006.01)
  *A61B 17/17* (2006.01)
  *A61F 2/44* (2006.01)
  *A61B 17/56* (2006.01)
  *A61F 2/30* (2006.01)
  *A61B 17/00* (2006.01)

(52) U.S. Cl.
  CPC ...... *A61B 17/7062* (2013.01); *A61B 17/7067* (2013.01); *A61F 2/4455* (2013.01); *A61F 2/4684* (2013.01); *A61B 2017/00526* (2013.01); *A61B 2017/568* (2013.01); *A61B 2034/108* (2016.02); *A61F 2/442* (2013.01); *A61F 2002/30578* (2013.01); *A61F 2002/4658* (2013.01)

(56) References Cited

U.S. PATENT DOCUMENTS

| | | | |
|---|---|---|---|
| 8,998,909 B2 | 4/2015 | Gillman et al. | |
| 9,039,772 B2* | 5/2015 | Park | A61B 17/7062 623/17.16 |
| 9,211,128 B2 | 12/2015 | Gillman et al. | |
| 9,414,846 B2* | 8/2016 | Gillman | A61B 17/154 |
| 9,414,938 B2 | 8/2016 | Gillman et al. | |
| 2004/0092932 A1 | 5/2004 | Aubin et al. | |
| 2005/0085719 A1* | 4/2005 | Franklin | A61B 90/11 600/424 |
| 2010/0217336 A1 | 8/2010 | Crawford et al. | |
| 2011/0144760 A1* | 6/2011 | Wong | A61F 2/38 623/20.14 |
| 2011/0214279 A1* | 9/2011 | Park | G06T 7/0012 29/592 |
| 2012/0041445 A1* | 2/2012 | Roose | A61B 17/1746 606/96 |
| 2012/0116562 A1* | 5/2012 | Agnihotri | A61B 17/155 700/98 |
| 2012/0296339 A1* | 11/2012 | Iannotti | A61F 2/46 606/87 |
| 2013/0172731 A1 | 7/2013 | Gole | |
| 2014/0180430 A1 | 6/2014 | Gillman et al. | |
| 2016/0030067 A1 | 2/2016 | Frey et al. | |
| 2016/0058577 A1 | 3/2016 | Gillman et al. | |
| 2016/0113784 A1* | 4/2016 | Robichaud | A61F 2/4657 606/102 |

* cited by examiner

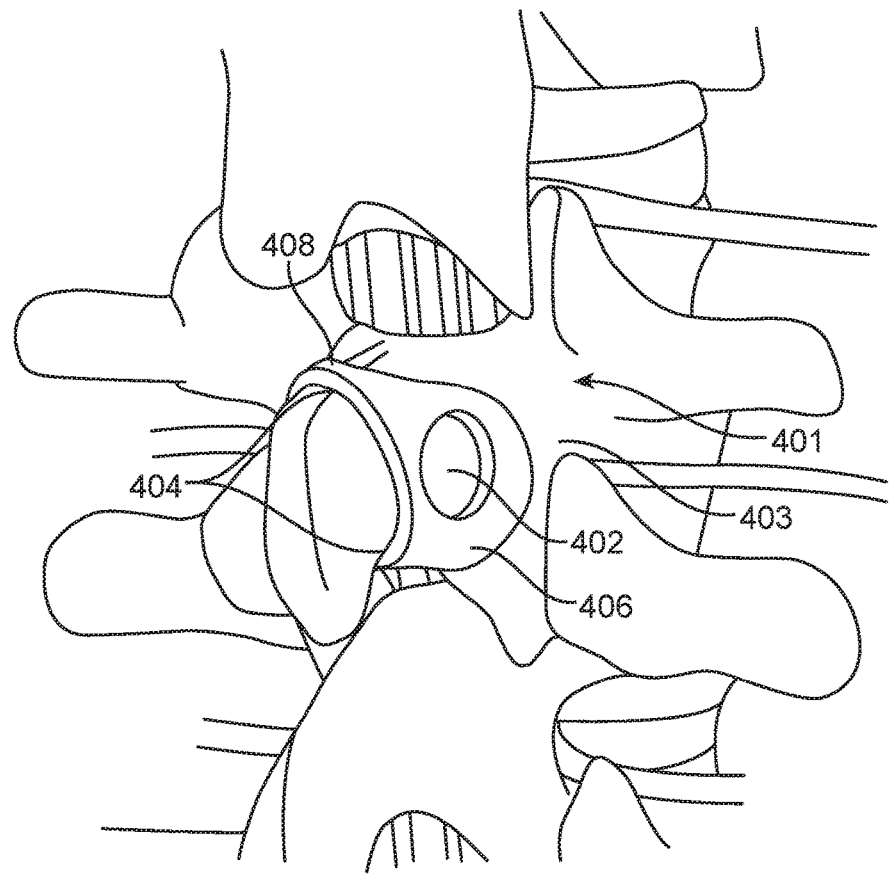
FIG. 4A
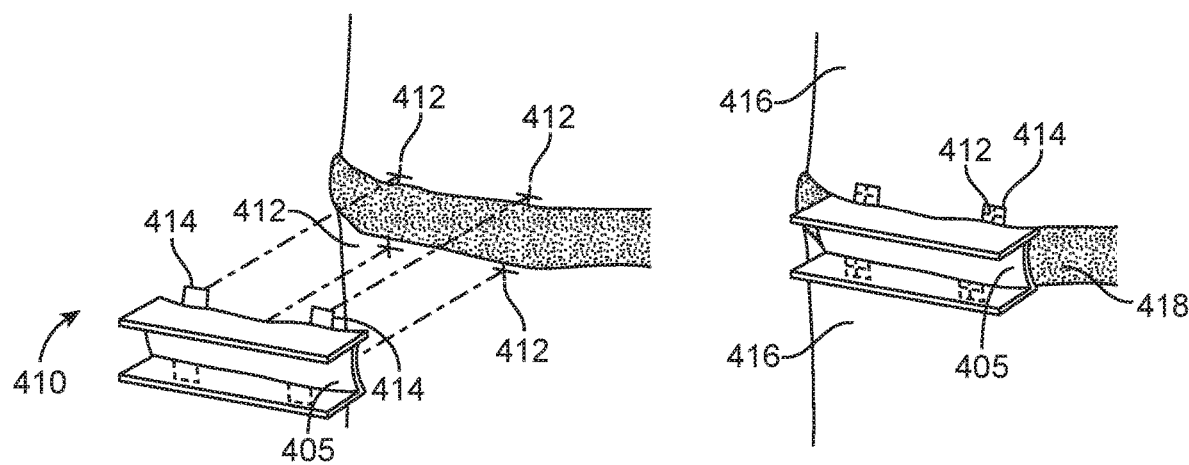
FIG. 4B
FIG. 4C

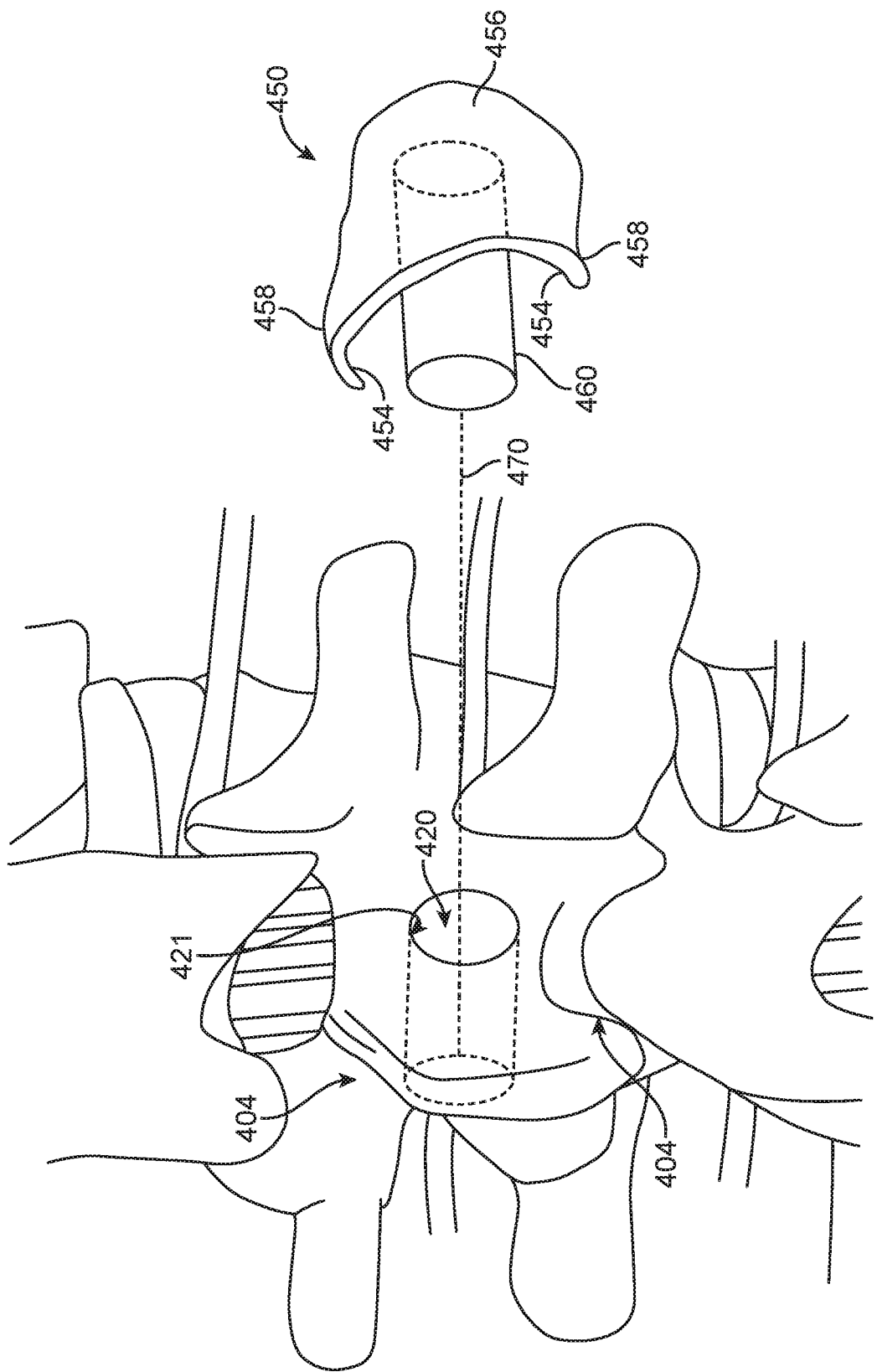

METHODS TO ASSIST WITH MEDICAL PROCEDURES BY UTILIZING PATIENT-SPECIFIC DEVICES

CROSS-REFERENCE

This application claims the benefit of U.S. Provisional Application No. 62/360,828, filed Jul. 11, 2016, which application is incorporated herein by reference.

BACKGROUND

Technical Field

The present disclosure relates to methods to assist with performing medical procedures, such as spinal procedures, and more particularly, to methods of manufacturing and using devices based on computer generated imaging of a patient's unique tissue structure to achieve accurate resection of portions of tissue and for, in some instances, accurate placement of implants or other devices.

Description of the Related Art

While there are many potential surgeries that a doctor can perform on a patient, each with their own inherent risks and complications, spinal procedures are often carry some of the greatest risks. Generally speaking, there are four categories of procedures that surgeons use to alleviate common spine issues in patients: decompressions, spinal fusion, disc replacements, and deformity corrections. Specific surgeries in each category are typically performed from certain approaches to the spine of the patient due to limitations that make access easier from one approach over another. The possible approaches include an anterior, posterior, or lateral surgical approach. In other words, certain procedures are more easily performed from the front, rear, or side of the spine, respectively. In addition, spinal surgery may be performed in any part of the patient's spine, including the cervical spine, or neck; the thoracic spine, or middle portion of the back; or the lumbar spine, or lower back.

Decompression procedures are used in patients who experience pain as a result of the spinal cord or nerves being squeezed by a piece of the spine or disc that is out of place and can include operations such as a discectomy, laminectomy, foraminotomy, or corpectomy, among others. Each of these procedures often includes removal of part or all of the lamina on a vertebra of the patient, and may, at times, includes removal of lamina on more than one vertebra. However, it is rarely the case that the lamina itself is causing the patient to experience pain, instead the lamina, or part of the lamina, is removed to break the continuity of the rigid ring of the spinal canal in order to allow the soft tissues within the canal to expand and/or change shape, thus decompressing the affected area. In other decompression procedures, such as with a discectomy, the doctor first removes all or part of the lamina in order to gain access to another area of the spine, such as a disc. Then, the surgeon can separate other soft tissue to expose the disc and remove the portion of the disc that is compressing the nerves.

In some situations where the vertebrae are damaged and can no longer move properly, such as with arthritis, fractures of a vertebra, or as a follow-up surgery for a patient with a severely herniated disc, spinal fusion may be desired. While these procedures may or may not include removal of a part of the vertebra or disc, fusion typically includes installing a graft that attempts to mimic the normal healing process of bones by integrating with sequential vertebra as the bone heals, resulting in two or more vertebra permanently joined together to move as one. The grafts may include a fusion cage, bone autograft from the patient's body, a bone allograft from cadaver bone, or a synthetic graft produced with synthetic materials. After placing the graft, the graft is then secured with implants that will vary based on the location of the procedure, such as standard plates and screws placed from the front of the spine, pedicle screws placed from the rear of the spine, rods through screws placed from the rear of the spine, or fusion cages placed from the front or the side of the spine. Either standard sized or patient specific implants may be used.

Yet other patients may be treated with a full disc removal and replacement if the issues with that patient's disc or discs are more serious than a herniation. A disc replacement involves replacing the entire disc with a prosthesis designed to imitate the functions of a normal disc, namely carry load and allow for a proper range of motion. The surgeon first removes the disc and then, in some instances, locates additional areas to be removed in the disc cavity to provide for grooves or channels or other features that allow for installation of the prosthesis. The disc replacement prosthetic may include two plates with a compressible, plastic-like piece between the plates. The prosthesis may be installed and secured by attaching one plate to the vertebra above the disc being replaced and the other to the vertebra below, with the surfaces of the plates that attach to the vertebrae having tines or notches that slide into channels cut or drilled onto the surface of the vertebrae facing the prosthesis. As such, these prosthetic devices are secured to the vertebrae and allow a full range of motion in the disc cavity, similar to a healthy spine. The plates may be standard sized, generic plates, or patient specific plates.

Finally, circumstances may arise that call for a correction to a deformity in a patient's spine, such as with an osteotomy, which is a procedure where a doctor removes bone of the patient and forces the spine closed with hardware in a new orientation in order to fix the deformity. While there are several types of osteotomies, one example procedure is the Smith-Petersen Osteotomy, which includes removing a wedge of spinal structure from the rear section of the spine and then lengthening the anterior portion to force the wedge closed with hardware. In some circumstances, the discs may be intentionally ruptured and new material added to the front of the spine to assist with the mobility of the spine after forcing the rear side of the spine closed.

Each of these four categories of operations can be aided by computer generated data derived from CT, MRI, or other scans, such as X-rays. Using these imaging sources, surgeons can more effectively determine the area to be removed from a patient's spine and the proper alignment and positioning for installation of any implants through 3-D modeling and rendering. Based on these 3-D models, some doctors use lasers or peripheral guide pins during medical procedures in an attempt to measure the adequacy of tissue removal or to guide the hardware; however, devices in the art are relatively complex and do not carry a high level of accuracy, which increases the chances of complications for a patient in complex surgeries like spinal procedures.

Because the potential risks of a procedure on the spine are so great, surgeons generally use tools that increase accuracy while being relatively easy to use and manipulate. For example, with procedures where part of the spinal structure is removed, such as the lamina or a disc, it is crucial that the surgeon only remove the correct portion of the lamina in the correct orientation according to the patient's specific spinal structure and kinetics. Otherwise, removing too much or too little of the lamina may render the surgery ineffective or create additional issues for the patient, such as longer recovery times and expansion of the soft tissue of the spinal canal into an unwanted area. Furthermore, installation of grafts or other implants may call for an even higher level of accuracy, as improper placement of such devices may prevent the graft from taking hold or may cause undue restriction of the movement of the patient following the procedure, rendering the surgery ineffective in either situation. Disc replacements have similar issues wherein the surgeon must correctly install the implant in the correct location or risk having the implant fail to carry load and provide movement. It is also possible for any improperly placed implant to slip out of place, which may cause nerve damage and prevent mobility of the patient until a second operation can be performed. With respect to deformity corrections, some recent studies provide a more objective basis of inherent risks by suggesting that the chance of major complications following osteotomies can be around 30%, even with the best surgeons and the best hospital resources. Of course, the risks with any procedure are only increased when performed by less skilled doctors at less equipped hospitals. As such, surgeons and patients alike will benefit from increased accuracy when undergoing medical procedures.

SUMMARY

A method for creating at least one patient-specific device is disclosed. The method may include, as an example embodiment, generating a spine surface image from two or three dimensional image data of a spinal structure of a patient. From the spine surface image, an operation position can be determined that identifies an ideal operation location on or around the spine of the patient. The spine surface image can also be used to generate an operation image that may display the desired outcome of a spinal procedure. This operation image can then be superimposed over the spine surface image and aligned with the operation position to identify the portions of the spine for removal as well as, in some embodiments, installation locations for any hardware or implants. Then, a first image can be generated and superimposed over the spine surface image that shows a first device configured to align with the operation position and the spine of the patient in order to accurately identify and allow access to an area of the spine that is to be removed during the procedure. Then, a second image can be generated and similarly superimposed and aligned that displays a second device, configured in some embodiments to measure the adequacy of the removal identified by the first image. In other embodiments, the second image may also show a device arranged to identify and allow access to the installation locations for hardware or implants predetermined from the operation image. Finally, the method may also include generating control data from the first and second images that controls operation of a machine configured to produce the devices shown in the first and second images, respectively.

A method for performing surgeries using at least one device personalized to each patient is also disclosed. The method may include, for example, determining a size and a shape of an ideal amount of tissue to be removed from the spine of a patient prior to operation. After identifying the ideal tissue to be removed, a surgeon can then position a first personalized device adjacent to the spine of the patient and align the first personalized device to contact at least one surface of a vertebra in a position substantially aligned with the operation position for the procedure. The first personalized device, once aligned, allows the surgeon to identify and remove a portion of the spine in an extraction area. In some embodiments, a second personalized device is configured to have a size and a shape substantially similar to at least one vertebra after removal of the ideal amount of tissue. By placing the second personalized device adjacent to the extraction area and aligning the second personalized device with the operation position, the user can compare the outcome of the procedure with the ideal outcome determined prior to the procedure. In other embodiments, the second personalized device may be configured to identify and allow access to installation locations for hardware or implants. In yet other embodiments, a third personalized device may be used to measure the accuracy of the installation of hardware or implants, such as, for example, by having recesses with a size and a shape substantially similar to a final installation location for the hardware or implants according to the operation position.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 4A is a perspective view illustrating a patient-specific device formed according to one embodiment which is configured to assist with resection of the lamina.

FIG. 4B is a perspective view illustrating a patient specific device formed according to one embodiment which is configured to measure the adequacy of removal of a bulging or herniated disc portion.

FIG. 4C is a perspective view illustrating a patient specific device formed according to one embodiment which is configured to measure the adequacy of removal of a bulging or herniated disc portion.

FIG. 4D a perspective view illustrating a patient-specific device formed according to one embodiment which is configured to confirm resection of the lamina.

DETAILED DESCRIPTION

As mentioned above, embodiments of the methods and systems disclosed herein are based at least in part on pre-operating (pre-operative) imaging and at least in part on surgical procedures based upon the pre-operative methods and systems. As is understood in the relevant art, pre-operative imaging has a number of different purposes and generally is performed in order to subsequently guide or assist in surgical procedures. Aspects of the present disclosure are directed to a system for designing and constructing one or more patient-specific devices for use in medical procedures, such as, for example, spinal operations in which a portion of tissue is resected and in some embodiments, an implant or other devices (e.g., surgical hardware) is installed. The referenced systems and methods are now described more fully with reference to the accompanying drawings, in which one or more illustrated embodiments and/or arrangements of the systems and methods can be shown. Aspects of the present systems and methods can take the form of an entirely hardware embodiment, an entirely software embodiment (including firmware, resident software, micro-code, etc.), or an embodiment combining software and hardware. Throughout this disclosure, the terms "patient-specific" and "personalized" refer to aspects that are customized in the present disclosure for each particular patient due to each patient's unique tissue structure and the specific goals of each patient in a given procedure. Similarly, the terms "extraction" and "resection" refer to removal of tissue from a patient and in certain aspects, may be used interchangeably.

Figure 1:
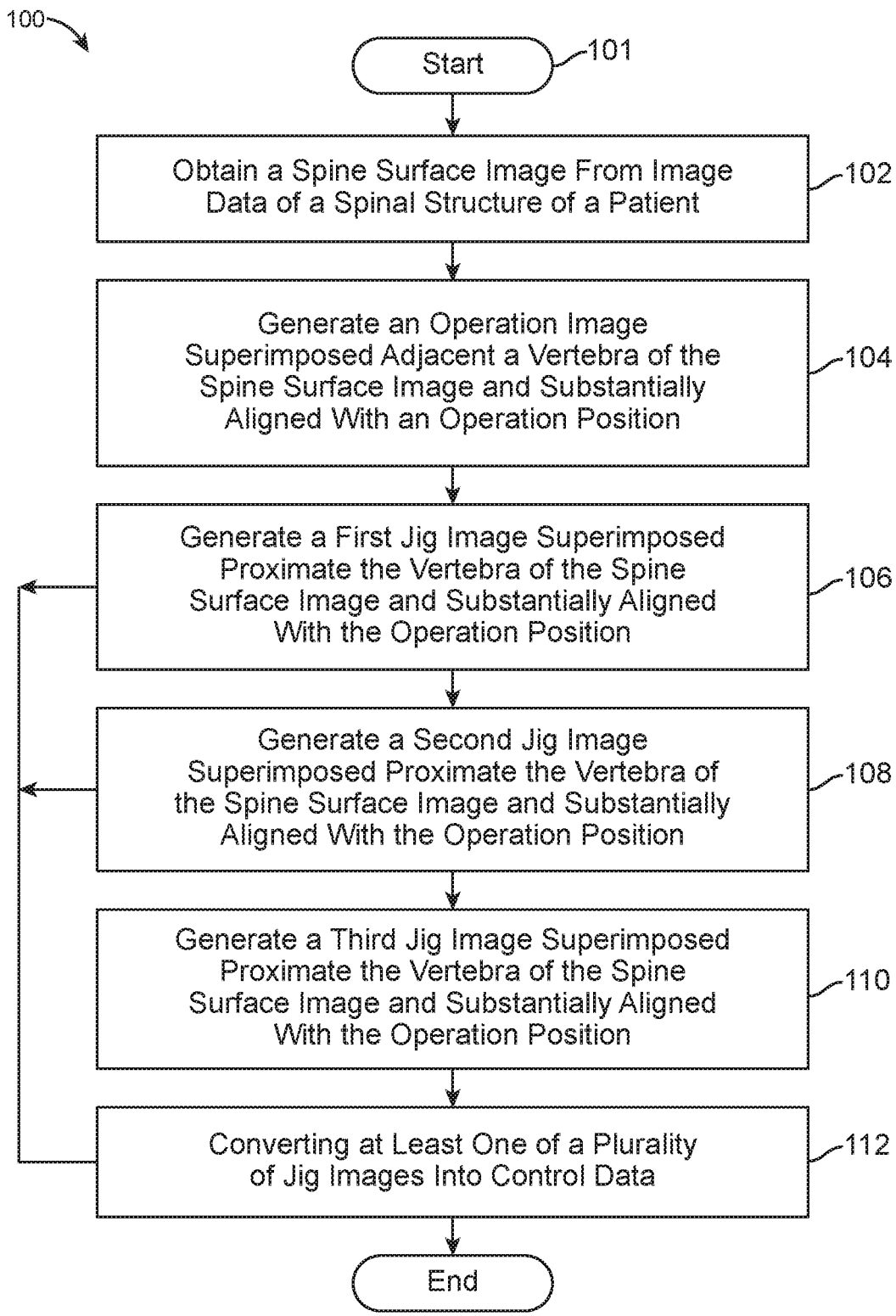
FIG. 1 is a flow diagram illustrating an example method for pre-operative imaging that includes converting imagery data from at least one of a plurality of patient-specific images into control data.

In FIG. 1, a method 100 according to an example embodiment for producing patient-specific device images and patient-specific devices starts at 101. At 102, an imaging machine generates a spine surface image from image data of a spinal structure of a patient. The image data used to generate the spine surface image at 102 can include image data from 2-D, 3-D or a combination of 2-D and 3-D sources, including, but not limited to X-ray computed tomography, computerized axial tomography, magnetic resonance imaging, or traditional x-ray images. At 104, a patient-specific device generator generates an operation image unique to the patient superimposed adjacent to at least one vertebra of the spine surface image. The operation image depicts a desired result from a spine surgery, which may include at least one ideal resection of a portion of the patient's spinal structure or in other embodiments, locating and installing at least one implant or other device (e.g., surgical hardware) after resecting a portion of the patient's spine. The operation image is substantially aligned with the spine surface image in an operation position, regardless of the physical orientation of the patient's spine. The operation position is determined prior to surgery and indicates a final alignment of the patient's spine based on the desired result of the surgery. The devices created from the present disclosure will be designed to assist the doctor in modifying the spine such that an actual result of the spinal surgery will be substantially similar to the desired result generated by the imaging machinery.

At 106, the patient-specific device generator generates a first patient-specific device image superimposed proximate the vertebra of the spine surface image and substantially aligned with the operation position. The first patient-specific device image may depict a first patient-specific device configured to identify and to allow access to a resection area during the spinal procedure. To ensure that the first patient-specific device is properly aligned with the operation position, the first patient-specific device image may include a plurality of contact portions, with each contact portion configured to contact a respective surface of at least one vertebra of the spine surface image. If only the first patient-specific device is used to achieve the desired result, as may be possible with simple resections, then a patient-specific device converter generates control data from the first patient-specific device image at 112 and ends.

Similarly, at 108, the patient-specific device generator may generate a second patient-specific device image superimposed proximate the vertebra of the spine surface image and substantially aligned with the operation position. The second patient-specific device image may be configured, in some embodiments, to measure if the resection area identified by the first patient-specific device image is substantially similar to the ideal resection portion or portions by having at least one confirmation portion and a plurality of contact portions. The plurality of contact portions may be formed to contact at least one of a plurality of contact surfaces wherein the plurality of contact surfaces can be configured to substantially align the second patient-specific device image with the operation position. Once aligned, the at least one confirmation portion may be configured to compare the resection area with the ideal resection portion. In some embodiments, the second patient-specific device image can also be configured to simultaneously identify and allow access to one or more installation locations that are predetermined from the spine surface image to represent a patient-specific configuration for installation of at least one implant. In some embodiments, the second patient-specific device image can also be configured to assist in guiding placement of the implant once the one or more installation locations have been identified and appropriate resections have been made to allow for installation of at least one implant.

If only two patient-specific devices are used to achieve the desired result, then a patient-specific device converter generates control data from at least one of the first patient-specific device image and the second patient-specific device image at 112 and ends. Alternatively, in embodiments where a third patient-specific device image is used, such as when the spinal procedure includes confirmation of the accurate installation of at least one implant, then the example method continues from 108 to 110. At 110, the patient-specific device generator generates a third patient-specific device image superimposed proximate the vertebra of the spine surface image and substantially aligned with the operation position. The third patient-specific device image is formed according to the desired result of the spinal procedure and may, in some embodiments, assist with at least one of placing at least one implant, determining adequacy of a final position and a final alignment of the spinal structure of the patient, and confirming that a placement of at least one implant installation substantially aligns with the operation image. In those embodiments where a third patient-specific device image is configured to assist with confirming the placement of at least one implant installation, the third patient-specific device image may be configured to have a body containing one or more recesses that are configured to receive at least a portion of the at least one implant that may extend above a surface of at least one vertebra. It is also possible to configure the third patient-specific device image to perform more than one or all of these assisting functions, depending on the desired result of the spinal procedure.

Once the patient-specific device generator generates one or more patient-specific device images from the first patient-specific device image at 106, the second patient-specific device image at 108 and/or the third patient-specific device image at 110, the patient-specific device converter converts at one or more patient-specific device images into control data at 112 and the example method ends. The control data may be originally produced in a form or may be processed to a form that allows the control data to control operation of a manufacturing machine (e.g., 3D printer) wherein the machine is configured to produce at least one patient-specific device from the control data that substantially embodies at least one of the first patient-specific device image, the second patient-specific device image, and the third patient-specific device image.

Figure 2:
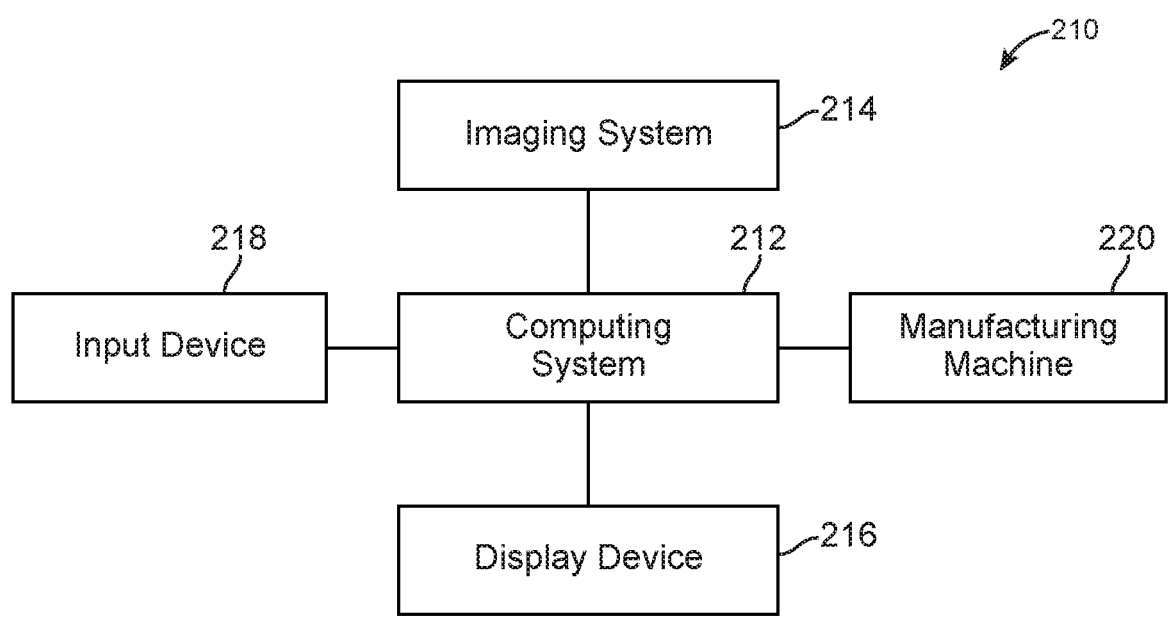
FIG. 2 schematically illustrates an example system of devices suitable for carrying out the example method of FIG. 1.

FIG. 2 shows an example embodiment of a simplified system 210 of devices for carrying out the methods of the present disclosure. The system 210 comprises a computing system 212 coupled to an imaging system 214 that captures and transmits patient image data to the computing system 212. The computing system 212 processes such data and transmits the data to the display device 216 for display of images and other data. An input device 218 receives input from a computer or an operator, such as a surgeon or a manufacturer, and transmits inputted information to the computing system 212 for processing. The imaging system 212 may include a spine or tissue imaging machine for forming image data from the spine or tissue structure of a patient. The computing system 212 may include a patient-specific device generator for processing and generating images, and a patient-specific device converter for generating design control data. A manufacturing machine 220 receives the control data from the computing system 212 for making patient-specific devices (also referred to herein as jigs). In some embodiments, the computing system 212 may further include instructions in the form of computer software for generating the spine surface image from image data obtained of the patient. Similarly, the computer system 212 may include instructions for generating and superimposing images of the desired result of the spinal procedure on the spine surface image and for generating and superimposing the plurality of patient-specific device images on the spine surface image. In some aspects, it may be desirable to input information into the input device 218 during preoperative planning such that the computer system 212 can direct the manufacturing machine 220 to create or alter the plurality of patient-specific images based on an understanding of the unique spinal structure of a particular patient as displayed on the display device 216.

Figure 3A:
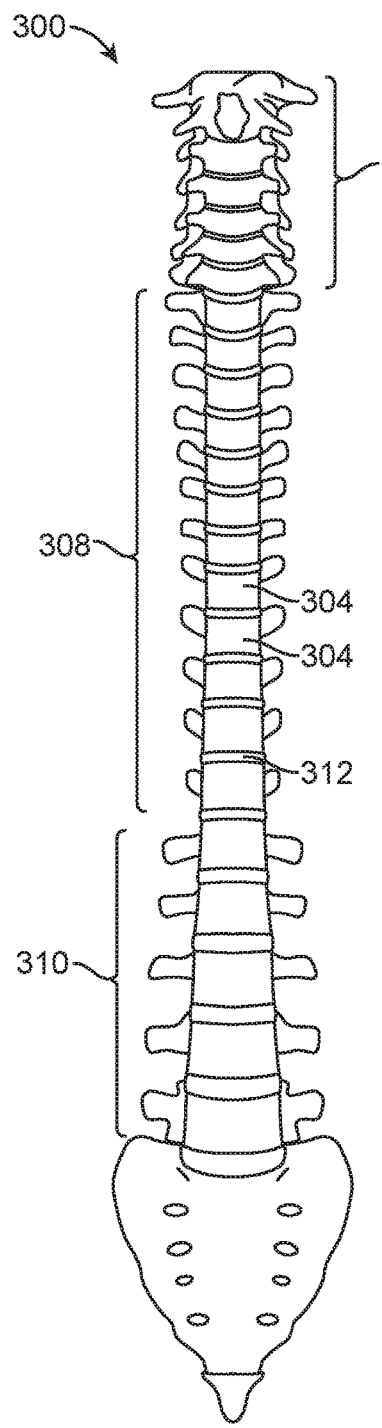
FIGS. 3A-3C illustrate the front, side, and rear views, respectively, of the typical human spine.
Figure 3B:
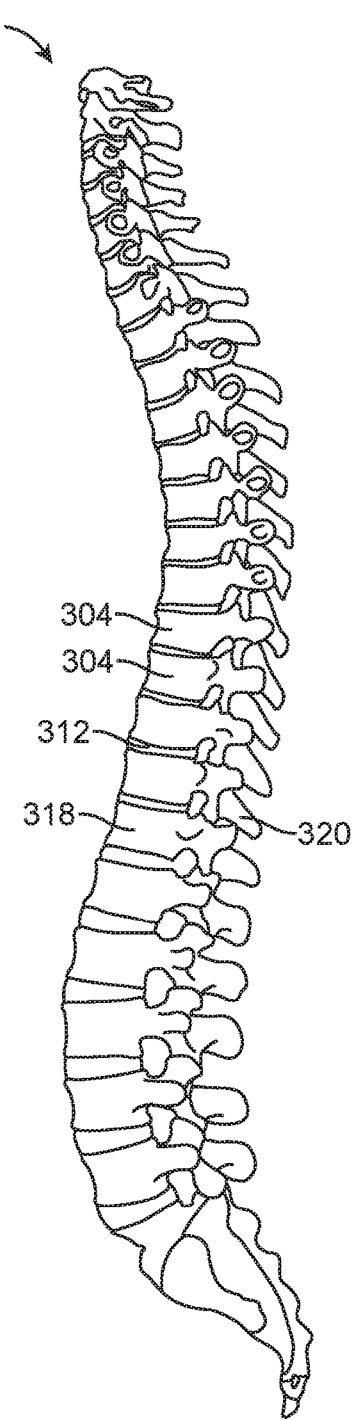
Figure 3C:
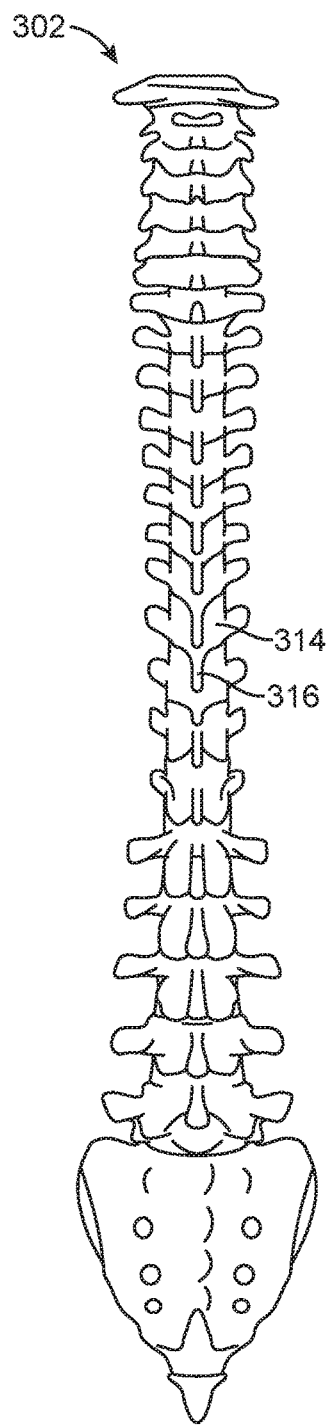

FIGS. 3A-C illustrate a simplified spinal structure of a human body from an anterior approach 300, a lateral approach 301, and a posterior approach 302 for reference. The spine is divided into three sections: a cervical spine 306, or neck; a thoracic spine 308, or middle portion of the back; and a lumbar spine 310, or lower back. Furthermore, FIGS. 3A-C illustrate a plurality of vertebrae wherein operations are typically performed on a series of two or more sequential vertebrae 304. Although not specifically labeled for efficiency, the plurality of vertebrae extend from either side of the sequential vertebrae 304 as clearly shown in FIGS. 3A-C. Sequential vertebrae, such as 304, are separated and connected by a disc 312 that allows for movement and rotation between the plurality of vertebrae. In addition to spinal procedures that can be performed from the anterior approach 300, lateral approach 301, or posterior approach 302, procedures are also common that involve resection of at least one of a portion of a spinal body 318, a lamina 314, a spinous process 316, a pedicle 320, or the disc 312 of the spinal structure of the patient. Common procedures include, as described above, spinal decompression, spinal fusion, disc replacement, and deformity correction procedures, among others. One skilled in the art would appreciate that any of the example embodiments of the methods disclosed herein can be adapted for use in any of the three approaches to the spine, whether anterior, lateral, or posterior. Similarly, the disclosed embodiments may be configured to assist with any of the above spinal procedures, among others, which may involve resecting any portion of the patient's spinal structure, including those not specifically labeled.

Personalized or patient-specific devices produced by the embodiments of the present disclosure or by other means may be used according to example embodiments of a method for using personalized devices to assist with spinal procedures.

One such embodiment is illustrated in FIG. 4A, which shows a first personalized device 401 having a body 406, an opening 402, and at least one contact member 408 sized and shaped to interface with the patient's spinal structure. According to the example method, a size and a shape of an ideal tissue extraction portion of a spinal structure of the patient are determined during pre-operative planning. Then, the first personalized device 401 is positioned adjacent to the spinal structure of the patient, such as adjacent a lamina 403 from a posterior approach. The first personalized device 401 is configured to contact at least a portion of one of a plurality of vertebra surfaces 404, although the first personalized device can be configured such that the body 406 contacts or aligns with a surface of a vertebra or vertebrae. In some embodiments, the at least one contact member 408 is configured to align the first personalized device 401 with the predetermined operation position such that the first personalized device identifies and allows access to an extraction area on the spinal structure of the patient through the opening 402. Ideally, the extraction area substantially embodies the ideal tissue extraction portion. The opening 402 can be configured to allow surgical tools or instruments to access the extraction area in order for the doctor to remove tissue from the extraction area.

Once the first personalized device 401 is properly aligned and contacting at least a portion of one of the plurality of vertebra surfaces 404, the doctor can then proceed to remove a portion of the spinal structure of the patient corresponding to the extraction area using the first personalized device 401 for assistance. After removing a portion of tissue corresponding to the extraction area, a second personalized device can be aligned with the extraction area, such as from an anterior approach. The second personalized device may be used, for example, to confirm the accuracy of the removed portion of the tissue. For instance, a second personalized device may be sized and shaped to interface with the spinal structure of the patient and may have a projection that is sized and shaped to be received within the cavity formed in the lamina with the assistance of the first personalized device shown in FIG. 4A.

One such embodiment is illustrated in FIG. 4D, which shows a second personalized device 450 having a body 456, a reference surface 460, and at least one contact member 458 sized and shaped to interface with the patient's spinal structure. According to the example method, a size and a shape of an ideal tissue extraction portion 420 of a spinal structure of the patient are determined during pre-operative planning. The first personalized device 401 assists with the removal of the extraction portion 420 and then, the second personalized device 450 is positioned adjacent to the spinal structure of the patient, such as adjacent a lamina 403 from a posterior approach. The second personalized device 450 is configured to contact at least a portion of one of a plurality of vertebra surfaces 404, although the first personalized device can be configured such that the body 456 contacts or aligns with a surface of a vertebra or vertebrae. In some embodiments, the at least one contact member 458 is configured with a contact surface 454 to align the second personalized device 450 with the predetermined operation position. The confirmatory surface 460 of the body may be configured to match the pre-operatively planned resection surface 421 of the extraction portion 420.

Once the second personalized device 450 is properly aligned and contacting at least a portion of one of the plurality of vertebra surfaces 404, the doctor can confirm the adequate removal of extraction portion 420.

In some embodiment, the second personalize device may be a set of devices including a go-device and a no-go-device. The go device being configured to match a minimum deviation from the pre-operatively planed extraction portion 420 and the no-go-device configured to match a maximum deviation from the preoperatively planned extraction portion 420. For example, in the embodiment shown in FIG. 4D a go-device may have a confirmatory surface 460 having a diameter representing the minimum diameter of the extraction portion 420 such that if the confirmatory surface 460 fits within or goes in the aperture formed by the extraction portion 420, then the diameter of the extraction portion 420 is greater than the minimum diameter. The no-go-device may have a confirmatory surface 460 having a diameter representing the maximum diameter of the extraction portion 420 such that if the confirmatory surface 460 does not fit within or does not go in the aperture formed by the extraction portion 420, then the diameter of the extraction portion 420 is less than the maximum diameter. Using a combination of the go and no-go devices can confirm that the extraction portion is within the tolerances determined during the pre-operative planning.

As another example, and with reference to FIGS. 4B and 4C, a second personalized device 410 may be formed with a body 405 having a size and a shape of at least a portion of the spinal structure of the patient after removal of the ideal tissue extraction portion, such as, for example, the removal of a bulging or herniated disc portion from between adjacent sequential vertebrae 416. Once aligned with the extraction area, the second personalized device 410 may be utilized to determine if the portion of the spinal structure removed (e.g., disc portion) is substantially similar to the ideal tissue extraction portion by engaging the second personalized device 410 with a plurality of contact locations 412 on the patient's spine.

In some embodiments, the body 405 of the second personalized device 410 may have a plurality of flanges 414 configured to assist in engaging the second personalized device 410 with the patient's spine to align with the plurality of contact locations 412. The plurality of flanges 414 may be configured to rest substantially flush with the spinal structure at the plurality of contact locations 412, as shown in FIG. 4C, such that the body 405 of the second personalized device 410 will contact at least one surface of the spinal structure of the patient (e.g., remaining disc structure) after removal of the tissue at the extraction area, or otherwise be spaced apart therefrom. For example, if the bulging or extruded disc is adequately removed, the flanges 414 of the body 405 of the second personalized device will be substantially flush with sequential vertebrae 416 and the body 405 may be flush or slightly offset from the remaining disc portion 418, as shown in FIG. 4C. In such a case, the tissue removed corresponding to the extraction area is confirmed as being substantially similar to the ideal tissue extraction portion, allowing the doctor to verify adequate tissue removal using the second personalized device. Conversely, if the flanges 414 are unable to properly seat or mate with the contact locations 412 due to interference or premature contact between the body 405 and remaining disc 418, it becomes evident that the extraction of tissue is inadequate or incomplete. In certain procedures, verification of adequate tissue removal corresponding to the ideal tissue extraction portion is enough to remedy the patient's issues, such as with a minor discectomy. However, in other procedures, more complete removal of a portion of the patient's spine may be desirable and in certain instances, the doctor must install at least one implant following removal of the spinal tissue.

Figure 5B:
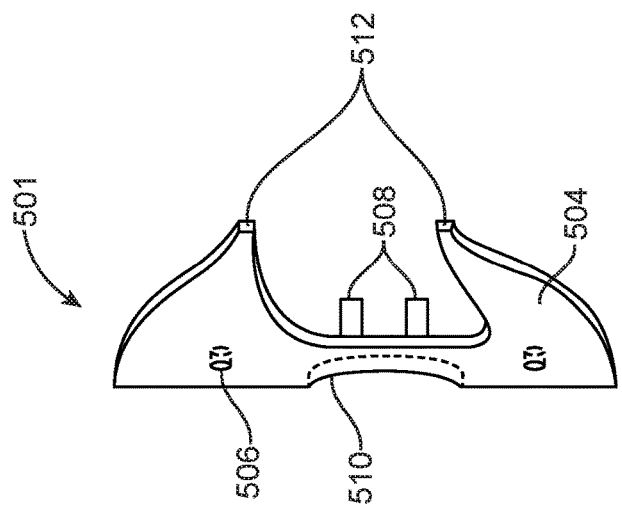
FIG. 5B is a side view of the patient specific device of FIG. 5A.
Figure 5A:
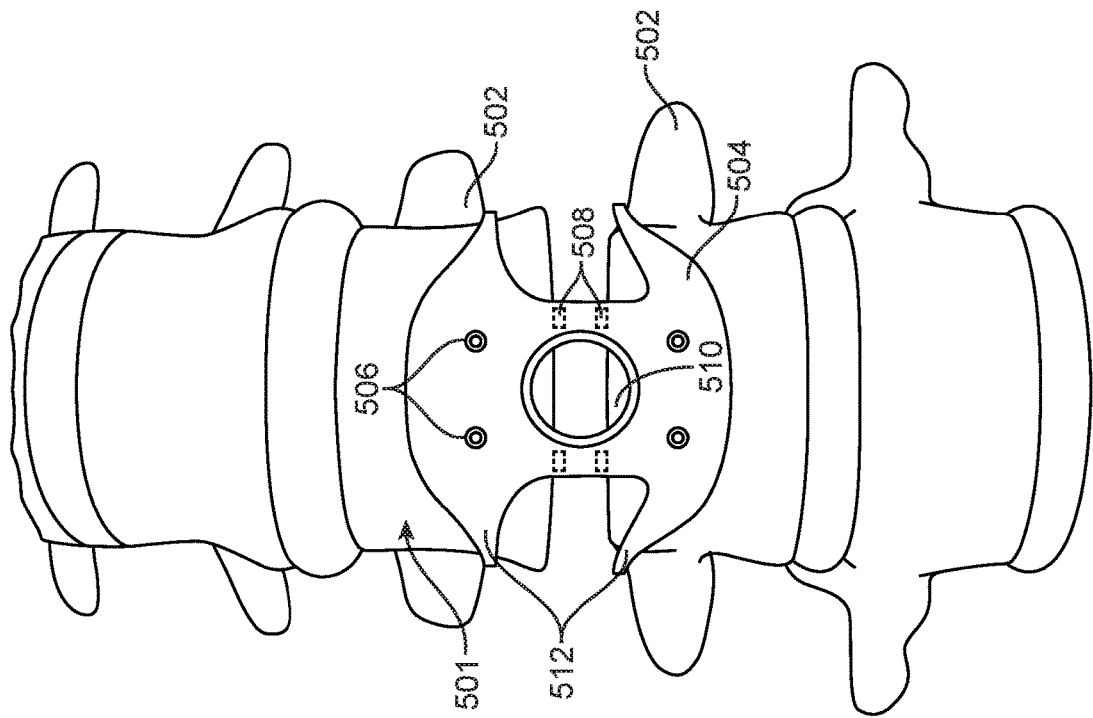
FIG. 5A is a front view of a patient specific device formed according to one embodiment which is configured to measure the adequacy of removal of disc tissue and to simultaneously identify and allow access to installation locations for at least one implant.

FIG. 5A shows an example embodiment of a second personalized device 501 aligned adjacent to the spine of a patient. The second personalized device 501 can be configured to align with an operation position by having one or more contact arms 512 configured to contact the spine at a plurality of contact locations, as described in other embodiments. In this embodiment and others, a first personalized device may have already been utilized to remove a portion of the patient's tissue, in this case a spinal disc. For efficiency and because one skilled in the relevant art would appreciate that the first personalized device may be configured with an expanded opening that allows for removal of an entire disc of the patient, such as in FIG. 5A, the first personalized device is not depicted as utilized in this embodiment.

In some embodiments, such as the example embodiment shown in FIGS. 5A and 5B, the second personalized device 501 may contain a body 504, a central placement hole 510 and a plurality of outer placement holes 506. The central placement hole 510 and the plurality of outer placement holes 506 may extend through the body 504 and can be configured to identify one or more placement locations. The placement locations can be generated from the predetermined operation location to correspond to a patient-specific location or locations for installation of at least one implant or at least one hardware member. In some embodiments, the central placement hole 510 and the plurality of outer placement holes 506 allow access to the tissue adjacent the holes so that portions of spinal tissue of the patient can be removed to allow for proper and accurate installation of the at least one implant or at least one hardware member. Examples of an implant for use in spinal procedures include a bone autograft, a bone allograft, a synthetic graft, or a replacement disc, although other options may be available. Furthermore, the hardware member may be one or more of standard or patient specific plates, screws, rods or fusion cages and one of ordinary skill in the relevant art would appreciate that the second personalized device 501 may be modified to assist with procedures from any of the three surgical approaches to the spine in any of the three sections of the spine, as the particular circumstances may dictate.

FIG. 5B depicts a side view of the second personalized device 501 from FIG. 5A to show the features of the second personalized device 501 in more detail. In particular, FIG. 5B shows how the second personalized device 501 may have a plurality of measurement members 508 configured to contact a surface of the spine above and below a removed disc. The plurality of measurement members 508 can also be arranged with a space between opposing pairs that represents the ideal tissue extraction portion identified by the first personalized device according to other embodiments of the present disclosure. As such, the second personalized device 501 can simultaneously identify and allow access to the placement locations to assist in installing at least one implant or at least one hardware member while also determining the adequacy of the resection following use of the first personalized device.

Figure 5D:
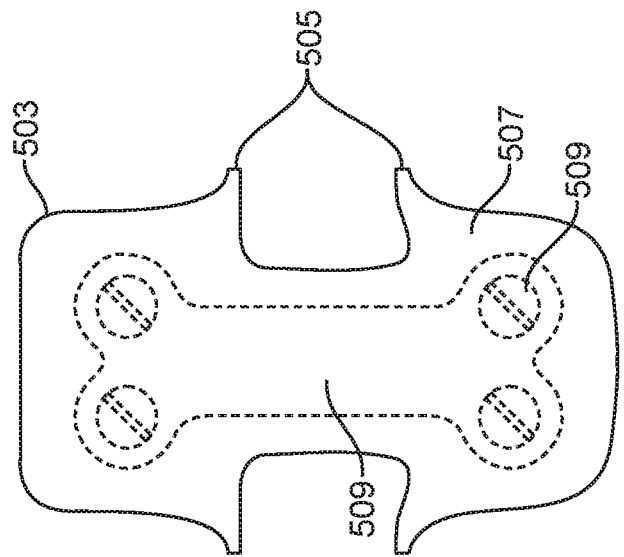
FIG. 5D is a rear view of the patient specific device of FIG. 5C.
Figure 5C:
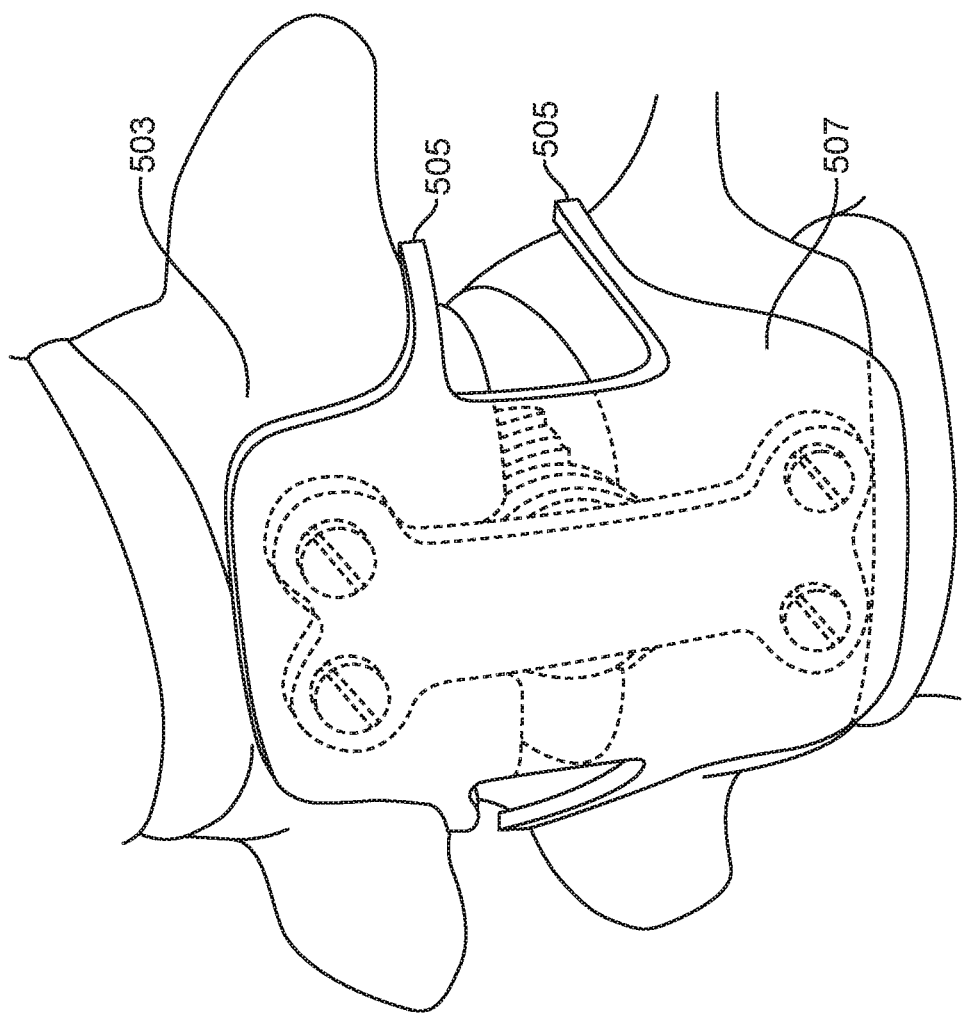
FIG. 5C is a perspective view of a patient specific device formed according to one embodiment which is configured to assist with installation of at least one implant by confirming final alignment of the spine and accuracy of the installation position of the implant.

After installation of at least one implant or at least one hardware member in the placement locations identified by the second personalized device 501, some embodiments of surgical methods may benefit from assistance by a third personalized device 503, as shown in FIGS. 5C-D. Similar to the other personalized devices of the present disclosure, the third personalized device 503 can be aligned with the predetermined operation location by having a plurality of contact members 505 configured to contact the plurality of contact locations. The plurality of contact members 505 can be further arranged to assist with determining the adequacy of a final spinal structure position and a final spinal structure alignment if the positioning between the plurality of contact members 505 is configured to be substantially similar to the positioning of the spinal structure following the ideal outcome of the spinal procedure. In other embodiments, the third personalized device 503 can assist with installing at least one implant or at least one hardware member, such as configuring the third personalized device to guide placement of the at least one implant or at least one hardware member.

FIG. 5D shows in more detail how it may also be possible to configure the third personalized device 503 with a body having a plurality of cavities 509 configured to receive at least one portion of at least one implant or at least one hardware member protruding from at least one surface of the plurality of vertebra surfaces of the spinal structure of the patient. In such a configuration, the third personalized device 503 will mate or nest with vertebra surfaces and the implant and/or hardware member if the installation of the implant and/or hardware member is proper. If the third personalized device 503 does not mate or nest as intended, then installation is deemed improper and the installation can be refined as desired, using one or more other personalized devices if desirable, until the third personalized device 503 confirms that placement is accurate.

Figure 6B:
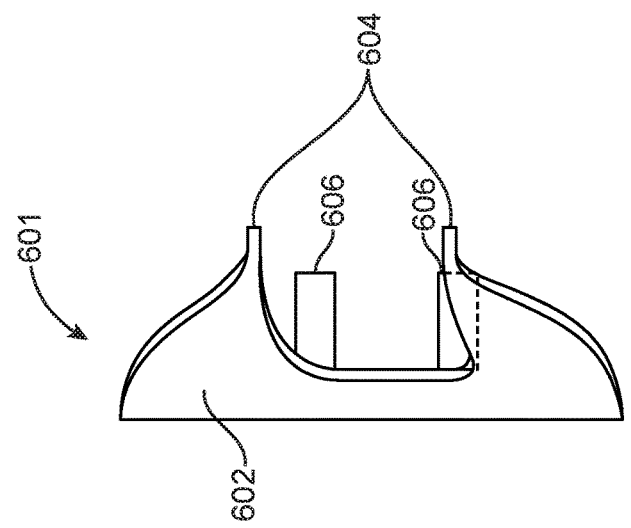
FIG. 6B is a side view of the patient specific device of FIG. 6A.
Figure 6A:
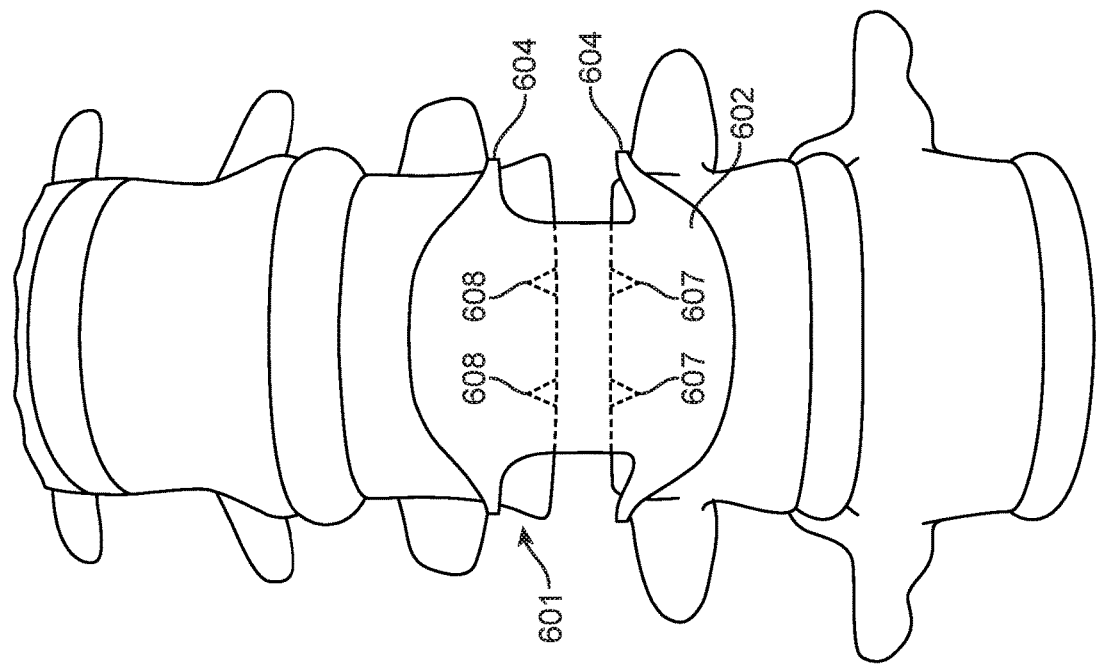
FIG. 6A is a front view of a patient specific device formed according to one embodiment which is configured to measure the adequacy of removal of disc and vertebral tissue.

FIGS. 6A-D show an alternative embodiment of the present disclosure adapted for use in a spinal fusion procedure wherein a first personalized device (or jig) may have already been utilized to remove a resection portion of tissue as described above. According to this embodiment, a second personalized device 601 can be provided with a body 602 and a plurality of contact flanges 604. Similar to other embodiments, the plurality of contact flanges 604 are configured to contact at least one surface of a vertebra of the patient's spine in order to align the second personalized device 601 with the predetermined operation position. In other embodiments, the second personalized device 601 may be configured to identify and allow access to a plurality of implant resection portions 608 that correspond to tissue to be removed prior to installation of at least one implant, in this case, a replacement disc. FIG. 6B shows a side view of the second personalized device 601 in more detail, particularly to emphasize how a plurality of implant measurement arms 606 can be configured to insert into a plurality of recesses 607 in the spinal structure of the patient following removal of the plurality of implant resection portions 608. In this way, the second personalized device 601 can measure the adequacy and accuracy of tissue removal prior to installing at least one implant or replacement disc.

Figure 6D:
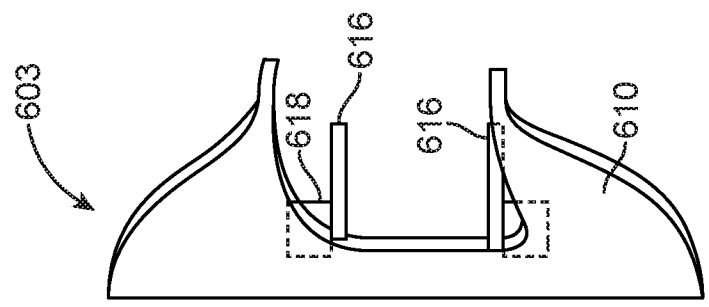
FIG. 6D is a side view of the patient specific device of FIG. 6C.
Figure 6C:
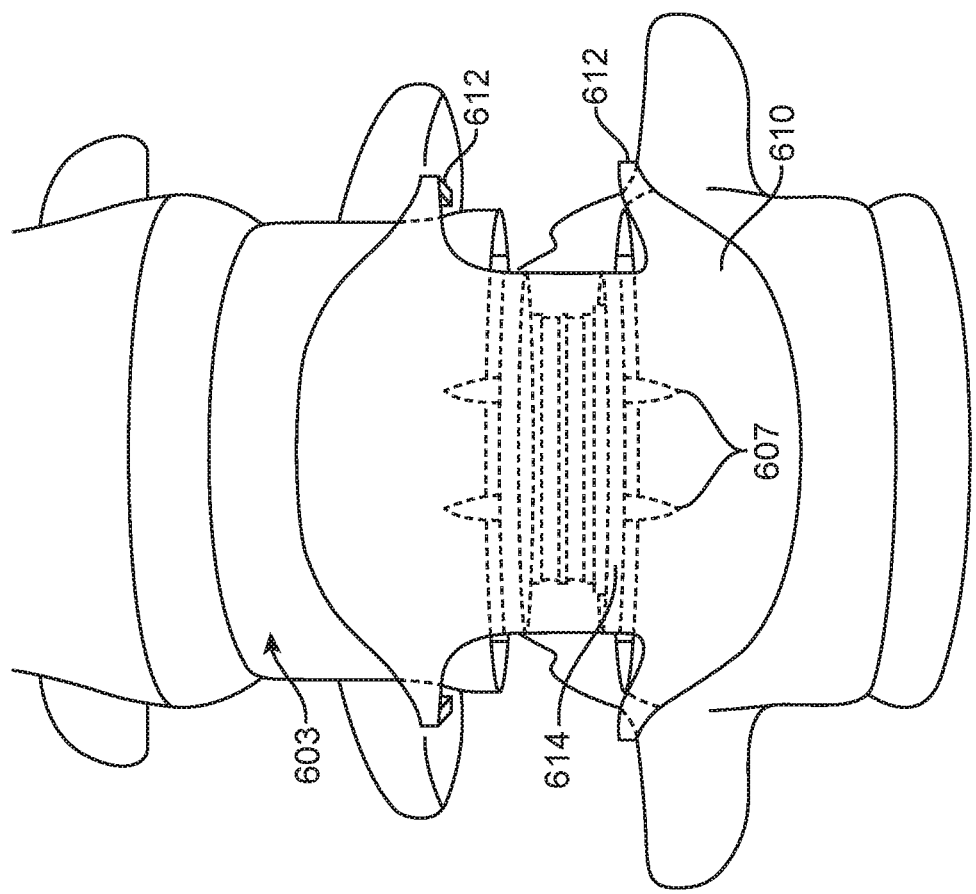
FIG. 6C is a front view of a patient specific device formed according to one embodiment which is configured to assist with installation of a replacement disc by confirming final alignment of the spine and accuracy of the installation position of the replacement disc.

Once the spinal structure has been resected to receive the replacement disc, FIGS. 6C-D show a third personalized device 603 with a body 610 and a plurality of contact flanges 612 arranged to align the third personalized device 610 with the predetermined operation position. In some embodiments, the third personalized device 603 can be configured to guide the placement of the replacement disc, while in other embodiments, the third personalized device can be configured to measure the adequacy of the placement of the implanted replacement disc. In order to measure the adequacy, the third personalized device 603 can include a plurality of measurement members 616 that insert into the plurality of recesses 607 to determine whether the replacement disc 614 has been inserted far enough into the spine of the patient. In addition, the third personalized device 603 can include a plurality of disc measurement arms 616 that are configured to contact the peripheral portions of the replacement disc itself. Because the third personalized device 603 is aligned with the operation position, one can conclude that the replacement disc 614 has been installed in the correct position and alignment if the plurality of disc measurement arms 616 contact a peripheral portion on opposing ends or sides of the replacement disc 614. However, if the replacement disc 614 is not properly installed (i.e., it does not properly mate or nest with the spinal structure and replacement disc 614), the third personalized device 603 can be removed and the spinal procedure refined, using one or more other personalized devices if desired until the replacement disc 614 is properly installed.

Figure 7A:
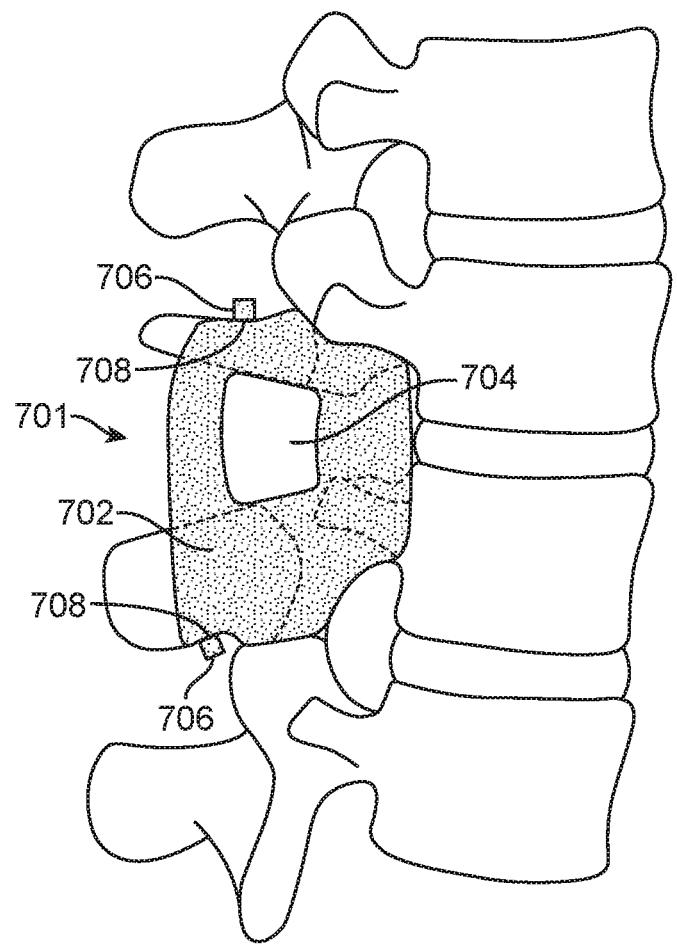
FIG. 7A is a side view of a patient specific device formed according to one embodiment which is configured to assist with removal of a portion of the spine corresponding to a unique deformity of the patient's spine.
Figure 7B:
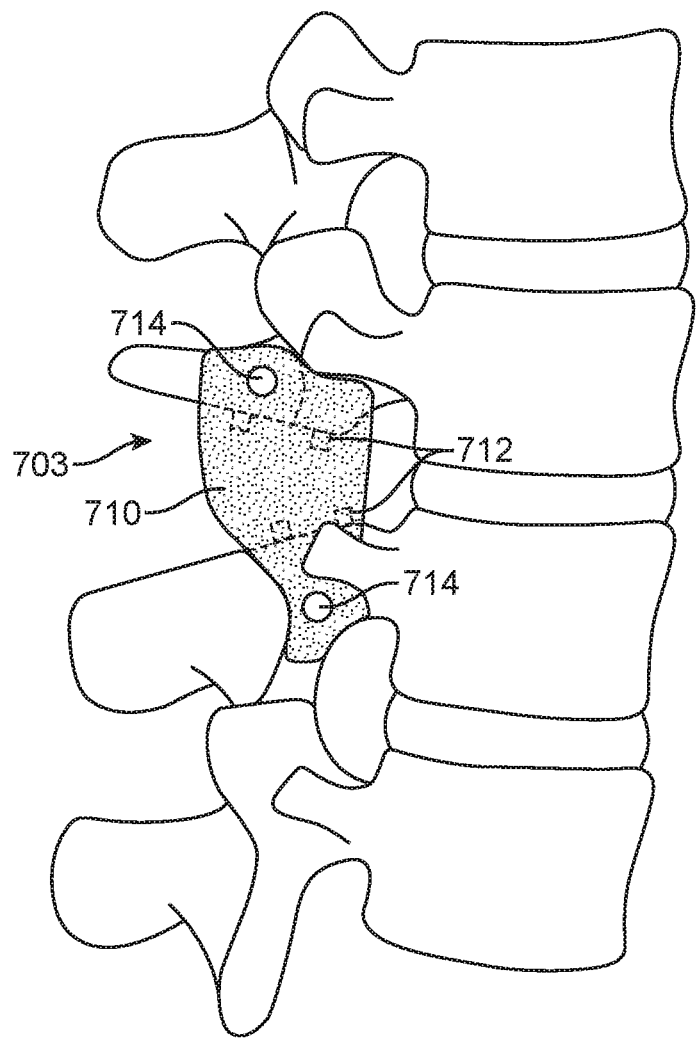
FIG. 7B is side view of a patient specific device formed according to one embodiment which is configured to measure the adequacy of removal of the portion of the patient's deformed spine while simultaneously identifying and allowing access to installation locations for at least one implant.
Figure 7C:
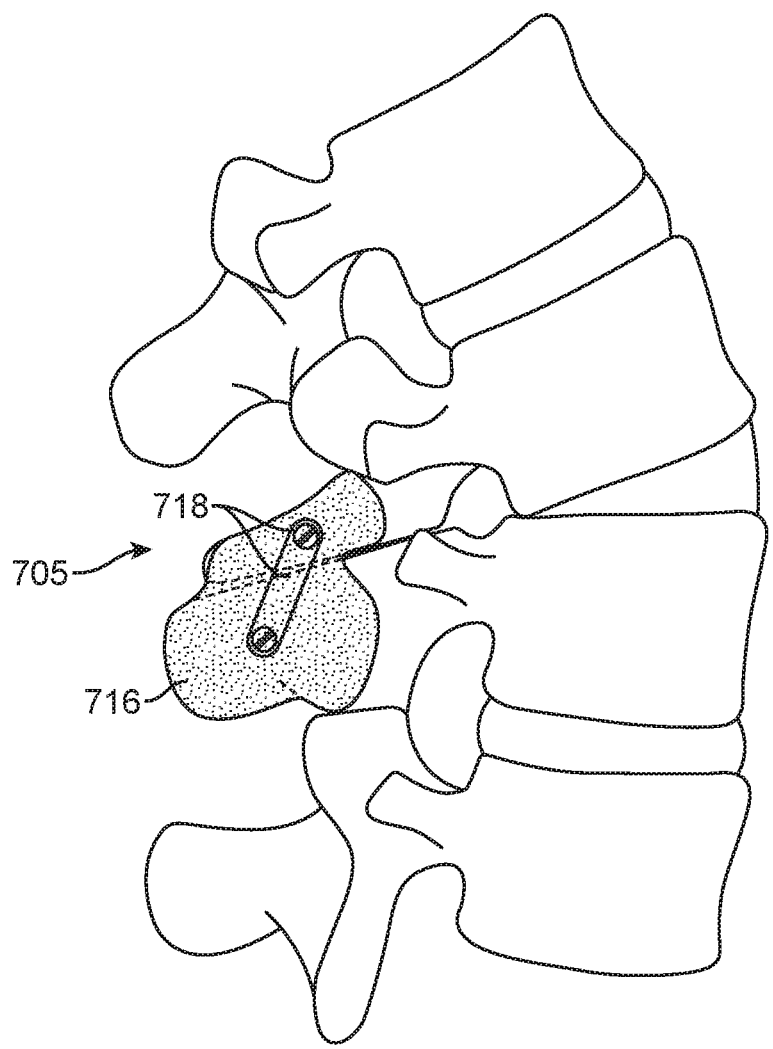
FIG. 7C is side view of a patient specific device formed according to one embodiment which is configured to assist with installation of at least one implant by confirming final alignment of the spine and accuracy of the installation position of each implant.

FIGS. 7A-C show an example embodiment of the present disclosure adapted for use in spinal deformity correction procedures wherein FIG. 7A illustrates a first personalized device 701 having a body 702, an extraction hole 704, and at least one contact member 706. The first personalized device 701 is positioned adjacent to the spinal structure of the patient and aligned with the predetermined operation position using the at least one contact member 706 as in other embodiments. Similarly, the first personalized device 701 can be configured to identify and allow access to an extraction area through the extraction hole 704 for removal of tissue corresponding to the extraction area.

After removing a portion of tissue corresponding to the extraction area using the first personalized device 701 for assistance (if desired), a second personalized device 703, can be aligned with the extraction area, such as from a lateral approach, as shown in FIG. 7B. The second personalized device 703 may be formed with a body 710 having a plurality of measurement members 712 arranged with a distance between opposing members that represents an alignment of the spine following removal of the ideal tissue extraction portion. If the plurality of measurement members 712 contact sequential vertebra at the plurality of predetermined contact locations, then adequate tissue has been removed. But, if adequate tissue has not been removed, then one may need to modify the tissue removed in the resection area, using the first personalized device 701 if necessary or desired. In other embodiments, the second personalized device 703 may include a plurality of installation holes 714 configured to simultaneously identify and allow access to placement locations on the spine for at least one hardware member. Similar to other embodiments, the plurality of installation holes 714 extend through the body 710 of the second personalized device 703 and may be configured to allow a doctor access for resection of tissue before installing at least one hardware member according the placement locations (e.g., drilling a pilot hole). In other embodiments, the plurality of installation holes 714 may be figured to allow the second personalized device 703 to guide placement of at least one hardware member.

Once the spinal structure has been resected to receive at least one hardware member, a third personalized device 705, as shown in FIG. 7C, can be aligned adjacent to the spine and configured to align with the operation position as in other embodiments to determine adequacy of the final spinal structure position and the final spinal structure alignment. In some embodiments, the third personalized device 705 can be configured to guide the placement of the least one hardware member, while in other embodiments, the third personalized device can be configured to measure the adequacy of the placement of the at least one hardware member. In assisting with confirming adequate placement of the at least one implant, the third personalized device 705 may have a plurality of cavities 718 configured to receive at least one portion of at least one hardware member protruding from at least one surface of the plurality of vertebra surfaces of the spinal structure of the patient. In such a configuration, the third personalized device 705 will mate or nest with the spinal structure and installed hardware if the installation of the hardware is proper. If the third personalized device 705 does not closely mate or nest with the spinal structure and installed hardware, then installation is improper and the installation can be refined as needing, using one or more other personalized devices if necessary or desired, until the third personalized device 705 confirms that placement is accurate and the spinal procedure has been successfully performed.

Figure 8:
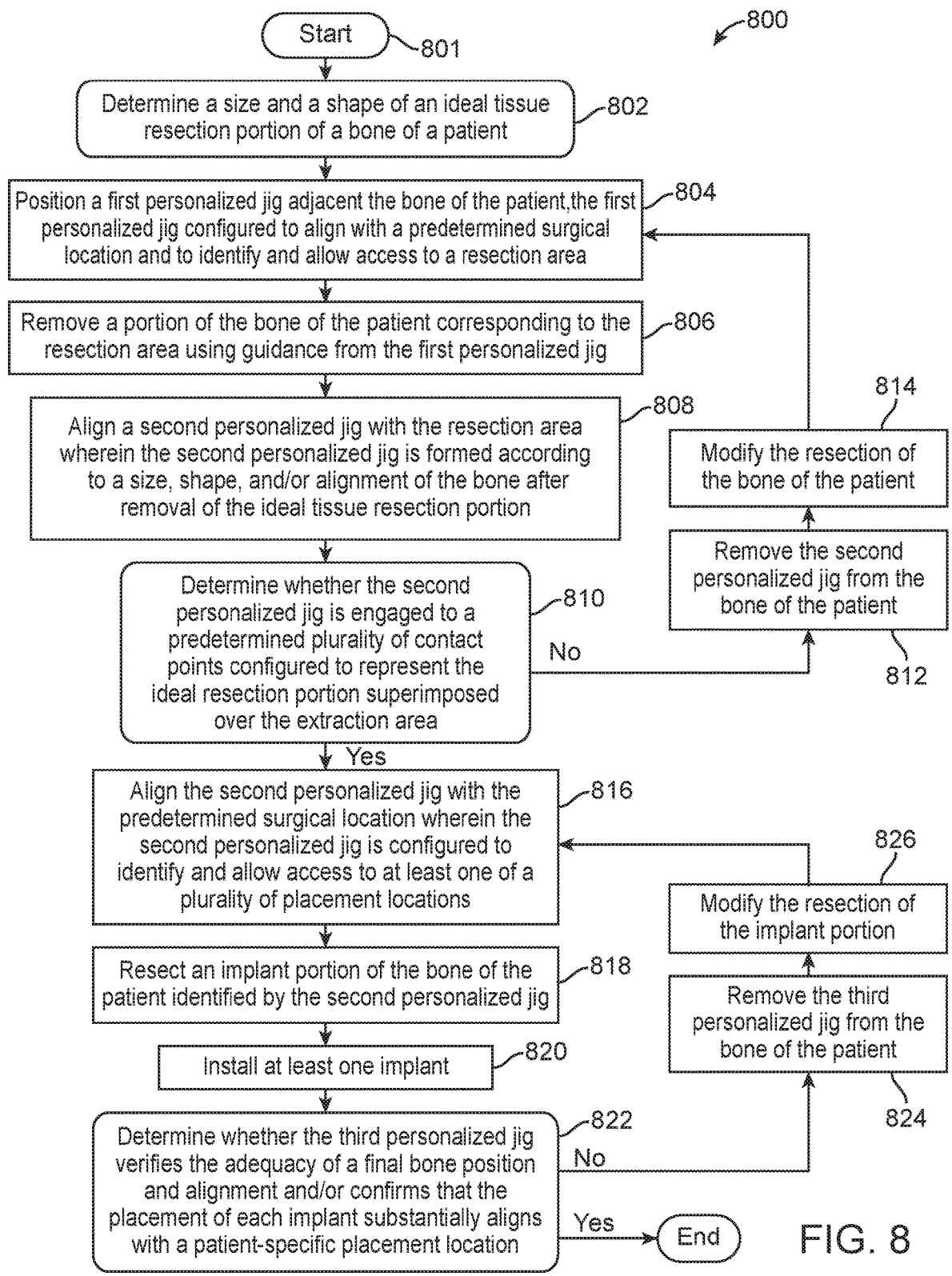
FIG. 8 is a flow diagram illustrating an example method for performing a medical procedure utilizing at least one patient specific device formed according to the embodiments disclosed herein.

One skilled in the art would also appreciate that the example embodiments of the disclosure can be adapted for more general use outside of spinal procedures, as depicted by the flow diagram in FIG. 8. In some aspects, it may be possible to adapt the methods disclosed to use patient-specific devices in any procedure where accurate resection of patient tissue is desired, which may include applications in cardiology, endovascular, veterinary and dentistry, among others.

According to FIG. 8, a method 800 is described by starting at 801 and proceeding to determine a size and a shape of an ideal tissue resection portion at 802. Then, a first patient-specific device (e.g., patient specific jig) is aligned with a predetermined procedure location adjacent the tissue structure of the patient at 804 wherein the first patient-specific device is configured to identify and allow access to a resection area. A portion of tissue can then be removed at 806 using the first patient-specific device for assistance. A second patient-specific device configured to represent the tissue structure following resection of the ideal resection portion can then be aligned with the predetermined procedure location at 808. At this point, it can be determined at 810 if the tissue removed in the resection area is consistent with the ideal tissue resection portion. If not, the second patient-specific device is removed at 812 and resection of the tissue is modified at 814 until adequate tissue has been removed. In some embodiments, the disclosed method can end after removal of tissue if removal of tissue is the desired result of the procedure. In other procedures, additional work may be desired, wherein the method proceeds to 816 with a second patient-specific device configured to identify and allow access to at least one of a plurality of placement locations. The doctor can then remove an implant portion of the tissue at 818 in order to install at least one implant at 820. In some embodiments, the second patient-specific device or a third patient-specific device may be used to guide placement of the at least one implant. In other embodiments, the third patient-specific device can configured to confirm the placement of the implant or the final tissue position following the procedure at 822. If the third patient-specific device does not confirm that the procedure was successful, the third personalized jig can be removed at 824 and the procedure can be modified at 826 until the third patient-specific device confirms accuracy of the procedure at 822 and the method ends.

Figure 9:
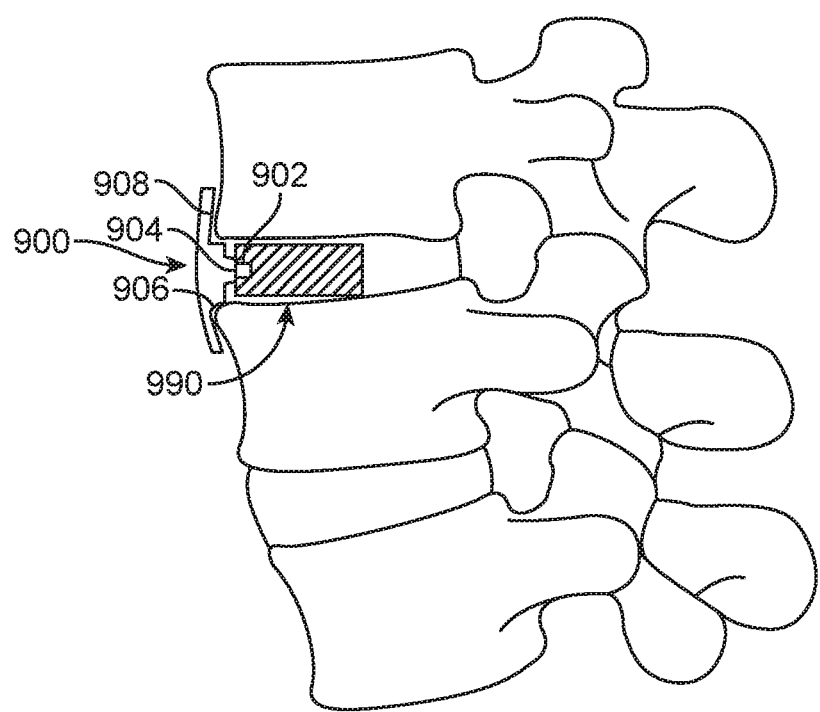
FIG. 9 is a side view of a patient specific jig for confirming placement of a fusion cage.

FIG. 9 is a side view of a patient specific jig 900 for confirming placement of a fusion cage. In some embodiments, the patient specific jig 900 can be configured to measure or confirm the adequacy of the placement of a hardware member, such as a fusion cage 990. In assisting with confirming adequate placement of the at least one fusion cage 990, the patient specific jig 900 may have one or more implant alignment members 904, 902 configured to receive at least one portion of at least one implant, such as the fusion cage 990. As shown in FIG. 9, the patient specific jig 900 includes an abutment alignment surface 904 and a lateral alignment surface 902. The abutment alignment surface 904 is configured to abut an end of the fusion cage 990 to, for example, confirm that the fusion cage is implanted at to the proper depth, based on preoperative planning and scans. The lateral alignment surface 902 is configured to mate with a lateral side of the fusion cage 990 such that it confirms proper lateral placement of the fusion cage 990.

The patient specific jig 900 also includes anatomic alignment members 908, 906. The anatomic alignment member 908 extends superiority along the spine and includes an alignment surface shaped to mate with a vertebrae superior to the installation position of the fusion cage. The patient specific jig 900 may also include a second alignment member 908 that a vertebrae inferior to the installation position of the fusion cage 990. In addition, in some embodiments, the patient specific jig 990 may include an anatomic alignment member 906 that extends between the inferior and superior vertebrae. The alignment member 906 may have first and second alignment surfaces shaped to mate with respective surfaces of the inferior and superior vertebrae. A distance between the first and second alignment surfaces may be configured such that the patient specific jig confirms a correct distance between adjacent vertebrae, according to pre-operative planning.

During use, if the patient specific jig 900 does not closely mate or nest with the anatomic spinal structure and installed hardware, then installation is improper and the installation can be refined as needing, using one or more other personalized devices if necessary or desired, until the patient specific jig 900 confirms that placement is accurate and the spinal procedure has been successfully performed.

Figure 10:
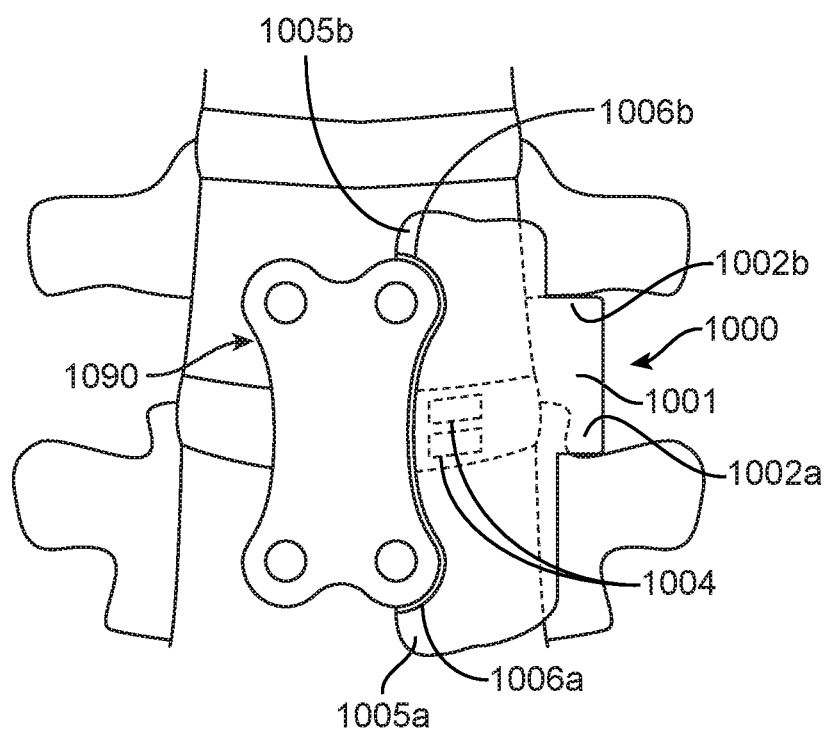
FIG. 10 is an anterior view of a patient specific jig for confirming placement of an anterior plate.

FIG. 10 is an anterior view of a patient specific jig 1000 for confirming placement of an anterior plate 1090. In some embodiments, the patient specific jig 1000 can be configured to measure or confirm the adequacy of the placement of a hardware member, such as an anterior plate 1090. In assisting with confirming adequate placement of the anterior plate 1090, the patient specific jig 1000 may have one or more implant alignment members 1005 configured to receive at least one portion of the implant 1090. As shown in FIG. 10, the patient specific jig 1000 includes abutment alignment members 1005a, 1005b. The abutment alignment members each include alignment surfaces 1005a, 1005b that are configured to abut an end or side wall of the anterior plate 1090 to, for example, confirm that the anterior plate is in the proper position and orientation, based on preoperative planning and scans. In some embodiments, the patient specific jig 1000 may include two or more abutment alignment members 1005a, 1005b. The two alignment members may work together to capture the implant 1090. For example, as shown in FIG. 10, a superior alignment surface 1006b and an inferior alignment surface 1006a each extend around respective ends of the implant 1090 such that the implant 1090 is captured between the alignment surfaces 1006a, 1006b.

The patient specific jig 1000 also includes anatomic alignment members 1001, 1004. The anatomic alignment member 1001 extends posteriorly along the spine and includes an alignment surfaces 1002a, 1002b shaped to mate with the vertebrae in a location posterior to the installation position of the anterior plate 1090. For example, the anatomic alignment member may mate with a surface of one or more pedicels.

In addition, in some embodiments, the patient anterior 1090 may include one or more anatomic alignment members 1004 that extend between adjacent inferior and superior vertebrae. The each alignment member 1004 may have an alignment surface shaped to mate with a surface inferior or superior surface of a vertebrae body. In some embodiments, the patient specific jig 1000 may include two alignment members 1004, each with a respective align surface shaped to match or nestingly mate with an inferior or superior surface of a vertebrae body. A distance between the respective alignment surfaces (either on a single alignment member 1004, or on two alignment members 1004) may be configured such that the patient specific jig confirms a correct distance between adjacent vertebrae, according to pre-operative planning.

During use, if the patient specific jig 1000 does not closely mate or nest with the anatomic spinal structure and installed hardware, then installation is improper and the installation can be refined as needing, using one or more other personalized devices if necessary or desired, until the patient specific jig 1000 confirms that placement is accurate and the spinal procedure has been successfully performed.

Figure 11:
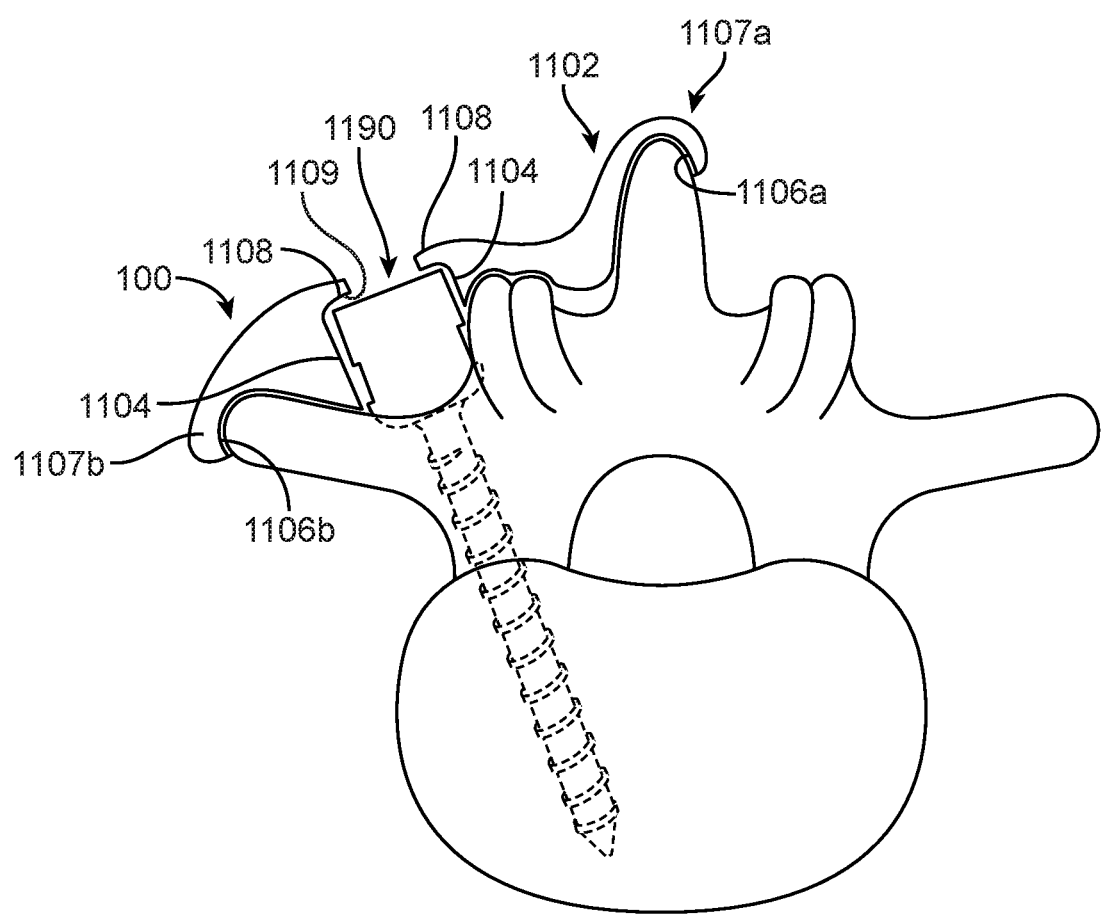
FIG. 11 is a top view of patient specific jig for confirming placement a posterior pedicle screw.

FIG. 11 is a top view of a patient specific jig 1100 for confirming placement a posterior pedicle screw 1190. In some embodiments, the patient specific jig 1100 can be configured to measure or confirm the adequacy of the placement of a hardware member, such as a pedicle screw 1190. In assisting with confirming adequate placement of the at least one pedicle screw 1190, the patient specific jig 1190 may have one or more implant alignment members 1108 and an alignment surface 1104 configured to receive at least one portion of at least one implant, such as the pedicle screw 1190. As shown in FIG. 11, the patient specific jig 1190 includes an abutment alignment surface 1109 on the implant alignment member 1108 and an alignment surface 1104, which may also abut or match the surface of the pedicle screw 1190. The abutment alignment surface 1109 is configured to abut an end of the pedicle screw 1190 to, for example, confirm that the pedicle screw 1190 is implanted at to the proper depth, based on preoperative planning and scans. The second alignment surface 1104 is configured to abut or mate with a side of the pedicle screw 1190, such as a side of the screw head, such that it confirms proper angular orientation of the pedicle screw 1190.

The patient specific jig 1190 also includes anatomic alignment members 1107a, 1107b. The anatomic alignment member 1107a extends posteriorly along the spine and includes an alignment surface shaped to mate with a surface of the vertebrae posteriorly to the installation position of the pedicel screw 1190. For example, the alignment member 1107a includes an alignment surface 1106a that nestingly mates with a surface of the spinous process.

The anatomic alignment member 1106a extends laterally along the spine and includes an alignment surface shaped to mate with a surface of the vertebrae lateral to the installation position of the pedicel screw 1190. For example, the alignment member 1107a includes an alignment surface 1106a that nestingly mates with a surface of the pedicle. In some embodiments, the alignment members 1107a, 1107b may extend from the body of the same patients specific jig 1100, while in other embodiments, the patient specific jig 1190 may include two bodies, each having a corresponding the alignment members 1107a, 1107b and implant aligment members 1108 and surfaces 1104.

During use, if the patient specific jig 1100 does not closely mate or nest with the anatomic spinal structure and installed hardware, then installation is improper and the installation can be refined as needing, using one or more other personalized devices if necessary or desired, until the patient specific jig 1100 confirms that placement is accurate and the spinal procedure has been successfully performed.

Aspects and features of the various embodiments described above can be combined to provide further embodiments. U.S. patent application Ser. Nos. 13/906,234; 14/166,605; 14/255,761; 14/521,031; 14/938,482; 14/485,074; and 14/521,031 are incorporated herein by reference, in their entirety. Aspects of the embodiments can be modified, if desired to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of using one or more patient-specific devices to assist in a spinal procedure, the method comprising:
   determining a size and a shape of an ideal tissue extraction of a spinal structure of a patient;
   positioning a first personalized device adjacent to the spinal structure of the patient, the first personalized device configured to contact at least a portion of one of a plurality of vertebra surfaces of the spinal structure of the patient in a predetermined operation position, the predetermined operation position arranged to define an extraction area of the spinal structure of the patient;
   removing a portion of the spinal structure of the patient corresponding to the extraction area defined by the first personalized device;
   aligning a second personalized device with the extraction area, the second personalized device formed according to a size and a shape of at least a portion of the spinal structure after removal of the ideal tissue extraction portion of the spinal structure of the patient; and
   utilizing the second personalized device to determine if the portion of the spinal structure removed corresponding to the extraction area is substantially similar to the ideal tissue extraction of the spinal structure of the patient by engaging the second personalized device with a plurality of contact points, the plurality of contact points predetermined to represent the ideal tissue extraction portion superimposed over the extraction area.

2. The method of claim 1 wherein the first personalized device is configured to allow access to the extraction area for operation of surgical tools on the extraction area.

3. The method of claim 1 wherein the second personalized device is configured to simultaneously identify at least one of a plurality of placement locations, the plurality of placement locations generated from the predetermined operation location to correspond to a patient-specific location for installation of at least one implant or at least one hardware member.

4. The method of claim 3, further comprising:
   installing at least one implant in the patient-specific location; and
   securing at least one hardware member to at least one portion of at least one vertebra, each hardware member configured to assist in coupling the implant to the spinal structure of the patient.

5. The method of claim 4 wherein installing at least one implant includes installing at least one of a bone autograft, bone allograft, synthetic graft, or replacement disc.

6. The method of claim 4 wherein securing at least one hardware member includes securing at least one of plates, screws, rods, or fusion cages.

7. The method of claim 1 wherein the first personalized device is configured to align with one of an anterior, posterior, or lateral approach to the spinal structure of the patient.

8. The method of claim 1 wherein positioning the first personalized device includes positioning the first personalized device in at least one of a cervical spine region, a thoracic spine region, or a lumbar spine region.

9. The method of claim 4, further comprising:
   aligning a third personalized device with the predetermined operation location after utilizing the second device, the third personalized device configured to assist with at least one of installing at least one implant or at least one hardware member, determining adequacy of a final spinal structure position and a final spinal structure alignment, or confirming that a placement of at least one implant or at least one hardware member aligns with the patient-specific location for installation by configuring the third personalized device to have a plurality of cavities, each of the plurality of cavities configured to receive at least one portion of at least one implant or at least one hardware member protruding from at least one surface of the plurality of vertebra surfaces of the spinal structure of the patient; and
   determining if the third personalized device is substantially aligned with the patient-specific location for installation of at least one implant.

10. The method of claim 9 wherein aligning the third personalized device includes aligning the third personalized device in an anterior position, a posterior position, or a lateral position of the spinal structure of the patient.

11. A method of using one or more patient-specific devices to assist in a medical procedure, the method comprising:
    positioning a first patient-specific device adjacent to a tissue structure of the patient, the first patient-specific device configured to mate with the tissue structure of the patient in a predetermined procedure location and to identify and to allow access to a resection area;
    resecting a portion of the tissue of the patient;
    aligning a second patient-specific device with the resection area, the second patient-specific device formed according to a size and a shape of at least a portion of the tissue structure after removal of an ideal tissue resection portion of the tissue structure of the patient; and
    utilizing the second patient-specific device to determine if the portion of the tissue structure removed is substantially similar to the ideal tissue resection portion of the tissue structure of the patient.

12. The method of claim 11, wherein the second patient-specific device is further configured to identify one or more patient-specific placement locations for installation of an implant or surgical hardware.

13. The method of claim 12, further comprising:
    installing an implant in the patient-specific placement location; and
    aligning a third patient-specific device with the predetermined procedure location, the third patient-specific device configured to assist with determining adequacy of a final tissue structure position and alignment, and/or confirming that a placement of the implant or surgical hardware aligns with the patient-specific location for installation; and determining if the third patient-specific device is substantially aligned with the tissue structure of the patient and the implant and/or surgical hardware.

* * * * *